US009320690B2

(12) United States Patent
Ontumi et al.

(10) Patent No.: US 9,320,690 B2
(45) Date of Patent: Apr. 26, 2016

(54) GELATIN ENCAPSULATED ORAL CARE COMPOSITION CONTAINING HYDROPHILIC ACTIVE, HYDROPHOBIC STRUCTURING AGENT AND OIL CARRIER

(75) Inventors: Dennis Kembero Ontumi, Easton, PA (US); Thomas James Boyd, Metuchen, NJ (US); Suman Kumar Chopra, Monroe, NJ (US); James Richard Brown, Edison, NJ (US)

(73) Assignee: Colgate-Palmolive Company, New York, NY (US)

( * ) Notice: Subject to any disclaimer, the term of this patent is extended or adjusted under 35 U.S.C. 154(b) by 205 days.

(21) Appl. No.: 13/995,543

(22) PCT Filed: Dec. 20, 2010

(86) PCT No.: PCT/US2010/061315
§ 371 (c)(1),
(2), (4) Date: Jun. 19, 2013

(87) PCT Pub. No.: WO2012/087280
PCT Pub. Date: Jun. 28, 2012

(65) Prior Publication Data
US 2013/0269133 A1  Oct. 17, 2013

(51) Int. Cl.
| *A61K 8/11* | (2006.01) |
| *A46B 11/00* | (2006.01) |
| *A61Q 11/00* | (2006.01) |
| *A61K 8/31* | (2006.01) |
| *A61K 8/37* | (2006.01) |
| *A61K 8/49* | (2006.01) |
| *A61K 8/81* | (2006.01) |

(52) U.S. Cl.
CPC .............. *A61K 8/11* (2013.01); *A46B 11/0003* (2013.01); *A61K 8/31* (2013.01); *A61K 8/375* (2013.01); *A61K 8/4926* (2013.01); *A61K 8/8111* (2013.01); *A61Q 11/00* (2013.01); *A46B 2200/1066* (2013.01)

(58) Field of Classification Search
USPC ................................................. 424/401, 456
See application file for complete search history.

(56) References Cited

U.S. PATENT DOCUMENTS

| 2,628,187 | A | * | 2/1953 | Frohmader et al. ........... 514/789 |
| 2,778,045 | A | | 1/1957 | Bly, Jr. et al. |
| 3,733,403 | A | | 5/1973 | Chen |
| 4,164,563 | A | | 8/1979 | Chang |
| 4,164,564 | A | | 8/1979 | Chen |
| 4,292,304 | A | | 9/1981 | Barels et al. |
| 4,422,985 | A | | 12/1983 | Morishita et al. |
| 4,426,337 | A | | 1/1984 | Suzuki et al. |
| 5,028,432 | A | | 7/1991 | Chopra et al. |
| 5,246,964 | A | | 9/1993 | Ueno |
| 5,254,346 | A | | 10/1993 | Tucker et al. |
| 5,300,305 | A | | 4/1994 | Stapler et al. |
| 5,390,984 | A | | 2/1995 | Boucherie et al. |
| 5,393,796 | A | | 2/1995 | Halberstadt et al. |
| 5,478,570 | A | | 12/1995 | Sunohara et al. |
| 5,533,791 | A | | 7/1996 | Boucherie |
| 5,538,974 | A | | 7/1996 | Ogawa et al. |
| 5,609,890 | A | | 3/1997 | Boucherie |
| 5,944,528 | A | | 8/1999 | Montgomery |
| 6,135,274 | A | | 10/2000 | James |
| 6,214,813 | B1 | | 4/2001 | Zhang et al. |
| 6,306,435 | B1 | | 10/2001 | Chen et al. |
| 6,384,033 | B1 | | 5/2002 | Ikeda et al. |
| 6,397,860 | B1 | | 6/2002 | Hill, II |
| 6,514,558 | B2 | | 2/2003 | Cardinaels |
| 6,524,558 | B2 | | 2/2003 | Kleinberg et al. |
| 6,905,673 | B2 | | 6/2005 | Rajaiah et al. |
| 7,348,306 | B2 | | 3/2008 | Araki et al. |
| 7,601,002 | B2 | | 10/2009 | Milanovich et al. |
| 7,628,999 | B2 | | 12/2009 | Sunkara |
| 7,722,274 | B2 | | 5/2010 | Hohlbein et al. |
| 7,727,565 | B2 | | 6/2010 | Jani et al. |
| 7,736,629 | B2 | | 6/2010 | Kamath et al. |
| 7,772,258 | B2 | | 8/2010 | Ina et al. |
| 7,807,141 | B2 | | 10/2010 | Huang et al. |
| 2002/0106234 | A1 | | 8/2002 | Johnson |

(Continued)

FOREIGN PATENT DOCUMENTS

| CN | 2164720 | 5/1994 |
| CN | 1592583 | 3/2005 |

(Continued)

OTHER PUBLICATIONS

Biokyowa, Inc., 2007, "L-Arginine Material Safety Data Sheet," pp. 1-5.
Biokyowa, Inc., 2010, "L-Arginine Free Base Certificate of Analysis".
Chemical Abstracts, "L-Arginine," Technical Information, CAS No. 74-79-3, retrieved from internet 2010.
Freund Industrial Co. Ltd., 2010, Spherex-Labo Seamless Mini-Capsule Laboratory Machine.
International Search Report and Written Opinion in International Application No. PCT/US10/061315, mailed Nov. 5, 2012.
International Specialty Products, 1999, "Gantrez Copolymers Technical Profile" pp. 1-15.
ISP Chemicals LLC., 2009, "Gantrez® S-97 BF Material Safety Data Sheet," pp. 1-5.

(Continued)

*Primary Examiner* — Walter Webb

(57) ABSTRACT

An encapsulated oral care composition includes: (a) a gelatin capsule; and (b) a oral care composition contained within the capsule, and including: (i) a hydrophilic active; (ii) a hydrophobic structuring agent; and (iii) an oil carrier. The hydrophilic active is preferably cetylpyridinium chloride. The hydrophobic structuring agent is preferably a gelled mineral oil. The oil carrier is preferably a vegetable oil. A method of cleaning teeth includes applying to the teeth the encapsulated oral care composition such that the capsule releases the oral care composition to clean the teeth. A oral care implement includes: a handle; a head mounted to the handle, the head having an outer surface and a plurality of tooth cleaning elements extending outwardly from the outer surface; and the encapsulated oral care composition positioned on the head.

16 Claims, No Drawings

(56) References Cited

U.S. PATENT DOCUMENTS

| | | |
|---|---|---|
| 2002/0176827 A1 | 11/2002 | Rajaiah et al. |
| 2004/0013723 A1* | 1/2004 | Parikh et al. .................. 424/456 |
| 2004/0208906 A1 | 10/2004 | Tatara et al. |
| 2004/0237226 A1 | 12/2004 | Hohlbein et al. |
| 2005/0084551 A1 | 4/2005 | Jensen et al. |
| 2005/0192348 A1 | 9/2005 | Bar-Or et al. |
| 2005/0207997 A1 | 9/2005 | Dixit et al. |
| 2005/0260266 A1 | 11/2005 | Gebreselassie et al. |
| 2006/0045854 A1 | 3/2006 | Zaidel et al. |
| 2006/0122159 A1 | 6/2006 | Huq et al. |
| 2006/0134020 A1 | 6/2006 | Robinson et al. |
| 2006/0275225 A1 | 12/2006 | Prencipe et al. |
| 2007/0122359 A1 | 5/2007 | Wang et al. |
| 2008/0213730 A1 | 9/2008 | Prencipe et al. |
| 2009/0041859 A1 | 2/2009 | Mizutani et al. |
| 2009/0092562 A1 | 4/2009 | Zaidel et al. |
| 2009/0178219 A1 | 7/2009 | Hohlbein |
| 2009/0186090 A1 | 7/2009 | Zaidel et al. |
| 2009/0320224 A1 | 12/2009 | Hohlbein et al. |
| 2009/0320226 A1 | 12/2009 | Robinson et al. |
| 2010/0004432 A1 | 1/2010 | Miyakawa et al. |
| 2010/0015184 A1 | 1/2010 | Tuel |
| 2010/0087409 A1 | 4/2010 | Freehauf et al. |
| 2010/0210703 A1 | 8/2010 | Vontz et al. |
| 2010/0227867 A1 | 9/2010 | DeJovin et al. |
| 2010/0273876 A1 | 10/2010 | Seville et al. |
| 2010/0322988 A1 | 12/2010 | Prencipe et al. |

FOREIGN PATENT DOCUMENTS

| | | |
|---|---|---|
| DE | 2753526 | 6/1978 |
| EP | 1112756 | 7/2001 |
| EP | 1797866 | 6/2007 |
| JP | S59-86132 U | 6/1984 |
| JP | 2004-189749 | 7/2004 |
| JP | 2008-156269 | 7/2008 |
| RU | 2327401 | 6/2008 |
| WO | WO 99/06031 | 2/1999 |
| WO | WO 03/043518 | 5/2003 |
| WO | WO 2006/002806 | 1/2006 |
| WO | WO 2009/157956 | 12/2009 |
| WO | WO 2011/014415 | 2/2011 |

OTHER PUBLICATIONS

ISP Technologies, Inc., 2010, "Gantrez S-97 BF Certificate of Analysis," pp. 1-2.

Morishita Jintan Co., Ltd., 2007, Capsule Business Division, "JINTAN Seamless Capsule Technology," www.jintanworld.com.

Ofner et al., 1987, "Swelling studies of gelatin. II: Effect of additives." J Pharm Sci. 76(9):715-23.

Pharmaceutical Resources, 1989, "PlastigelTM 5 Plasticized Hydrocarbon Gel Product Data Sheet," pp. 1-10.

Pharmaceutical Resources, LLC, 2009, "Plastigel-5 Certificate of Analysis".

Thau et al., 1965, "A New Procedure for the Preparation of Polyethylene-Mineral Oil Gels," J. Soc. Cosmetic Chemists 16:359-363.

\* cited by examiner

GELATIN ENCAPSULATED ORAL CARE COMPOSITION CONTAINING HYDROPHILIC ACTIVE, HYDROPHOBIC STRUCTURING AGENT AND OIL CARRIER

FIELD OF THE INVENTION

The invention relates to encapsulated oral care compositions and oral care devices including same.

BACKGROUND OF THE INVENTION

Oral care compositions in the form of solid, semi-solid, or encapsulated compositions positioned within the bristles of a tooth brushing device are known Cetylpyridinium chloride (CPC) is an ingredient commonly employed as an antibacterial agent in oral care compositions, but not in gelatin encapsulated liquid oral care compositions.

Accordingly, it is desired to provide gelatin encapsulated liquid oral care compositions comprising CPC. It is further desired to provide oral care devices comprising gelatin capsules containing liquid oral care compositions comprising CPC.

BRIEF SUMMARY OF THE INVENTION

Various embodiments described herein satisfy the aforementioned needs, by providing gelatin encapsulated liquid oral care compositions containing CPC and oral care devices comprising same.

According to one aspect of the invention, an encapsulated oral care composition comprises: (a) a capsule comprising gelatin; and (b) a oral care composition contained within the capsule, wherein the oral care composition comprises: (i) a hydrophilic active; a hydrophobic structuring agent; and (iii) an oil carrier.

In certain embodiments, the hydrophobic structuring agent comprises a gelled mineral oil.

In certain embodiments, the hydrophobic structuring agent comprises the gelled mineral oil in an amount of 1-20 wt. % based on a total weight of the oral care composition.

In certain embodiments, the gelled mineral oil is a plastigel comprising polyethylene and mineral oil.

In certain embodiments, the oil carrier comprises at least one of a vegetable oil and silicone oil.

In certain embodiments, the oil carrier comprises a C6 to C12 triglyceride.

In certain embodiments, the oil carrier constitutes 60-80 wt. % of the oral care composition.

In certain embodiments, the hydrophilic active is cetylpyridinium chloride.

In certain embodiments, the hydrophilic active constitutes 0.05-5 wt. % of the oral care composition.

In certain embodiments, the oral care composition further comprises 5-25 wt. % of a flavoring agent and 0.1-5 wt. % of a sweetening agent.

In certain embodiments, the oral care composition further comprises at least one member selected from the group consisting of an abrasive, a foaming agent, a whitening agent, an anti-calculus agent, a tartar control agent, an anti-inflammatory agent, an anticaries agent, a flavoring agent, a sweetening agent and a colorant.

In certain embodiments, the hydrophilic active is cetylpyridinium chloride, the hydrophobic structuring agent is a gelled mineral oil, the oil carrier is caprylic/capric triglyceride, and the oral care composition further comprises hydrated silica, sorbitol, sucralose, glycerin, a colorant and a flavoring agent.

In certain embodiments, the oral care composition has a viscosity from 150 to 330 cps.

According to another aspect of the invention, a method of cleaning teeth comprises applying to the teeth the encapsulated oral care composition of the invention such that the capsule releases the oral care composition to clean the teeth.

According to still another aspect of the invention, a oral care implement comprises a handle; a head mounted to the handle, the head comprising an outer surface and a plurality of tooth cleaning elements extending outwardly from the outer surface; and the encapsulated oral care composition of the invention positioned on the head.

In certain embodiments of the oral care implement, the capsule is positioned within and surrounded by the cleaning elements.

DETAILED DESCRIPTION OF THE INVENTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% may include 9.5% or 10.5%, given the degree of error in measurement that will be appreciated and understood by those having ordinary skill in the art.

As used herein, terms "treatment" or "treating" are intended to include prophylaxis. The terms include amelioration, prevention and relief from the symptoms and/or effects associated with oral malodor. The terms "preventing" or "prevention" refer to administering the composition beforehand to forestall or obtund oral malodor. Persons of ordinary skill in the art of compositions for the treatment of oral malodor (to which the present method claims are directed) recognize that the term "prevent" is not an absolute term. Rather, the term is understood to refer to the prophylactic administration of a composition to diminish the likelihood or seriousness of a condition, and this is the sense intended.

An "orally acceptable amount" of a compound is an amount that is not harmful to a mammal when a composition containing such amount is retained in the mouth, without swallowing, for a period sufficient to permit application to an oral surface as provided herein. In general, such amount of the compound is not harmful even if the composition is unintentionally swallowed. An "orally acceptable carrier" denotes any vehicle or carrier that is not harmful to a mammal when such carrier is used in a composition that is retained in the mouth, without swallowing.

Formulated oral care compositions such as tooth pastes and gels contain a number of functional and active ingredients, each of which contribute to at least one desirable property. Properly formulated oral care compositions are suitable for regular use to promote oral health. Functional additives include foaming agents that disperse other ingredients and provide for delivery of the active and functional materials to the oral surfaces, and tartar control agents to prevent the formation of calculus on tooth surfaces, as well as aesthetic functional ingredients such as flavors and pigments. Active ingredients include anticaries agents that provide a source of fluoride ion upon use. Various compositions also contain compounds or components with antibacterial properties, for example to reduce the formation of plaque on the surfaces. Further active ingredients include those with anti-inflammatory properties for prophylaxis and treatment of conditions such as gingivitis. Other than flavors and pigments, preferred oral care compositions do not include any of the aforementioned oral care active components.

Throughout this description, the expression "oral care active" denotes a component that provides an active effect during an oral care treatment. Oral care actives include, but are not limited to foaming agents, antibacterial agents, whitening agents, anti-calculus agents, antimicrobial agents, tartar control agents, anti-inflammatory agents, and the like.

Cetylpyridinium chloride dissolved in ethanol and incorporated into a vegetable oil center core of a gelatin capsule created cosmetic instability as well as delivery issues. Without wishing to be bound by any theory, it is believed that the issues are caused by rapid migration of cetylpyridinium chloride into the gelatin capsule during the cooling stage of manufacturing, when all layers of the capsule are effectively liquid. This migration causes "fish eye" defects in the capsule, presumably due to the compromised gelatin structure. In addition, the amount of cetylpyridinium chloride delivered is hampered since about 90% of the cetylpyridinium chloride is permanently bound to the gelatin capsule and not released or dissolved during brushing.

The invention is based in part on the discovery that deactivation of cetylpyridinium chloride in a gelatin encapsulated oral care composition, and destabilization of the gelatin capsule can be prevented, reduced or delayed by suspending the cetylpyridinium chloride in an oil carrier containing a hydrophobic structuring agent, and subsequently incorporating the resulting oil carrier and suspended cetylpyridinium chloride into the gelatin capsule.

The hydrophobic structuring agent is, as the name implies, a hydrophobic ingredient, which increases the viscosity of the hydrophobic liquid. Gelled mineral oils are presently the most preferred examples of suitable hydrophobic structuring agents. The gelled mineral oil is preferably a blend of mineral oil and polyethylene, and most preferably PLASTIGEL 5, which is a blend of 5% polyethylene in mineral oil, and is available from Pharmaceutical Resources/Lyne Laboratories Inc. of Brockton, Mass. Other suitable plastigels can be prepared in accordance with the teachings of Thau et al., "A New Procedure for the Preparation of Polyethylene-Mineral Oil Gets," J. Soc. Cosmetic Chemists, 16, 359-363 (1965). Suitable hydrophobic structuring agents additional to gelled mineral oils, such as plastigels, can be identified by using the present disclosure as a guide.

In addition to the hydrophobic structuring agent, the oral care composition contains an oil carrier, such as vegetable oil and/or silicone oil. Medium chain triglycerides (MCTs) are preferred as the oil carrier. The oil carrier preferably constitutes 50-90 wt. %, more preferably 60-80 wt. %, and most preferably about 75 wt. % of the composition. MCTs are typically about 6 to about 12 carbons in length. MCTs can be vegetable oils. Caprylic/capric triglyceride is a non-limiting example of an MCT preferred for use in the invention.

The hydrophilic active preferably constitutes 0.0001-7 wt. % or 0.05-5 wt. % or 0.05-1 wt. % of the oral care composition. The hydrophilic active is preferably cetylpyridinium chloride.

In addition to the hydrophilic active, the hydrophobic structuring agent and the oil carrier, the oral care compositions may further contain one or more orally acceptable abrasives, flavorants, colorants, sweeteners, processing aids, and optionally water.

In certain embodiments, the oral care composition comprises, consists essentially of, or consists of 1 to 10 wt %, preferably 2.5 to 7 wt %, and most preferably 5 wt % high cleaning abrasive, such that the total amount of abrasive delivered per application is 2 mg to 8 mg, preferably 3 mg to 6 mg, and most preferably about 4 mg of abrasive. The high cleaning abrasive is present in an orally acceptable carrier. A small amount of small particle size abrasive provides an improved stain removal effect and occlusion effect.

It is preferred that the abrasive be selected from high cleaning silica, tetrasodium pyrophosphate (TSPP), sodium tripolyphosphate (STPP), and mixtures thereof. The abrasives typically have a weight mean particle size in the range 2 to 18 µm with at least 90% by weight of particles having a size below 20 µm, a Radioactive Dentine Abrasion (RDA) determined on an aqueous slurry of the silica powder of 90 to 230, a Pellicle Cleaning Ratio (PCR), when incorporated in a dental composition at 10% by weight, greater than 80, the ratio of PCR to RDA being in the range 0.4:1 to less than 1:1 and having a Plastics Abrasion Value (PAV) in the range of 1 to 20.

The preferred abrasives are silicas having a particularly effective ability to clean, which is demonstrated by relatively high PCR values exhibited at conventional RDA values in oral care compositions containing a relatively small amount of the silica. Although the PCR to RDA ratio is less than 1, the RDA value preferably is higher than conventional silicas with a higher PCR to RDA ratio and, when compared to these products, a higher PCR is achievable with the same quantity of silica. Plastics Abrasion Values are a measure of the amount of scratching produced on a surface by the silica and are therefore indicative of possible damage to teeth. The silicas useful possess a moderate PAY but high PCR, which indicates good cleaning without excessive damage.

The amorphous silicas useful preferably have an oil absorption, using linseed oil, in the range 70 to 150 cm$^3$/100 g and, more preferably, the oil absorption is in the range 75 to 130 cm$^3$/1.00 g. Also, the amorphous silica preferably has a BET surface area in the range 10 to 450 m$^2$g$^{-1}$, and, more preferably, the BET surface area is in the range 50 to 300 m$^2$g$^{-1}$.

The weight mean particle size of the silica can be determined using a Malvern Mastersizer™ and a preferred material may have a weight mean particle size in the range 5 to 10 μm. The particle size distribution and, hence, the proportion of particles having a size below any particular value can be determined by the same technique. For the amorphous silica, at least 90% of the particles by weight preferably have a size below 17 μm.

In a particular embodiment, the weight mean particle size of the abrasives useful in the embodiments is in the range of 3 to 7 μm, with at least 90% of the particles by weight having a size below 16 μm, preferably below 12 μm.

In a particular embodiment, the silica is in the form of particles of a size such that they are effective to occlude dentinal tubules. Thus, the silica particles preferably have an average diameter of 0.510 microns or 1-9 microns or 2-7 microns, with an average diameter below 5 microns being most preferred.

The Radioactive Dentine Abrasion (RDA) of the silicas has a value in the range 100 to 220. More commonly, the RDA has a value in the range 120 to 200 and, frequently, the RDA is above 140. Generally, silicas having a PAY above 15 will have an RDA above 120 and those having a PAY above 17 have an RDA above 140.

The PCR (measured in a dental composition at 10% by weight) of the amorphous silica is greater than 85, preferably greater than 90 and more preferably greater than 95. The PCR: RDA ratio is preferably in the range 0.5:1 to 0.9:1.

The amorphous silica preferably has a pH value, measured on a 5% by weight suspension, in the range 5 to 8, more preferably in the range 6 to 7.5. The amount of water present on the amorphous silica suitable for use in a dental composition, as measured by the ignition loss at 1000° C., is usually up to 25% by weight and preferably up to 15% by weight. Usually the ignition loss at 1000° C. is more than 4% by weight.

Colorants such as pigments and dyes may be used in the composition. Pigments include nontoxic, water insoluble inorganic pigments such as titanium dioxide and chromium oxide greens, ultramarine blues and pinks and ferric oxides. The pigments have a particle size in the range of 5-1000 microns, preferably 250-500 microns, and are present at a concentration of 0.5 to 3% by weight.

Dyes used are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of ethyl-[4-[[4-[ethyl-[(3-sulfophenyl)methyl]amino]phenyl]-(4-hydroxy-2-sulfophenyl)methylidene]-1-cyclohexa-2,5-dienylidene][(3-sulfophenyl)methyl]azanium), FD&C Blue No. 1 (disodium salt of dibenzyldiethyldiaminotriphenyl-carbinol trisulfonic acid of indigotin) and mixtures thereof in various proportions. Preferred dye concentrations range from 0.0005 to 1% of the total weight.

Any suitable flavoring or sweetening agent may also be incorporated in the second oral care component. Examples of suitable flavoring constituents include flavoring oils, as for example, oils of spearmint, peppermint, wintergreen, sassafras, clove, sage, eucalyptus, marjoram, cinnamon lemon, and orange, and methyl salicylate. Suitable sweetening agents include sucrose, sucralose, lactose, maltose, sorbitol, xylitol, sodium cyclamate, perillatine, and sodium saccharin. Suitably, flavoring materials are included in the oral care composition in an amount of 5% to 25% by weight, more preferably 10% to 20% by weight, and most preferably about 15% by weight. The sweetening agents may comprise 0.1 to 5% by weight, more preferably 0.25 to 2% by weight, and most preferably about 0.5% by weight of the oral care components.

The oral compositions optionally contain one or more other non-active ingredients. Non-limiting examples include diluents, bicarbonate salts, modifying agents, foam modulators, thickening agents, structuring agents, pigmenting agents, sweetening agents, flavorants and colorants. Tooth pastes, tooth gels, and other oral care compositions are formulated with these and optionally other additives according to known principles.

The oral care composition is encapsulated in a gelatin capsule. Encapsulating liquid or aqueous compositions in a gelatin capsule can be accomplished using techniques known in the art and described in, for example, U.S. Pat. Nos. 4,422,985, 4,426,337, 5,478,570, The process typically entails forming a jet of the oral care composition and a jet of the coating material (e.g., gelatin) coaxial with the jet of oral care composition, heating the coaxial jets (optionally with a third coaxial heating element or hot air) and introducing the components into a cooling liquid to form capsules formed of the oral care composition, coated with the gelatin. The components are prepared by mixing the components of the core in one container and the components of the shell in another container. The capsule materials are heated to provide a fluid medium. The core and capsule materials are then pumped separately to a two-fluid nozzle submerged in an organic carrier medium. The capsules formed are allowed to cool and stiffen. They are then denatured and separated for further handling. Although the oral care composition is preferably prepared in the absence of alcohol, any alcohol present in the oral care preferably is evaporated during the heating of the respective components. Preferably, the gelatin comprises from 6 to 15% of the total weight of the encapsulated oral care composition (i.e., the capsule and the oral care composition), more preferably 8 to 12%, and most preferably about 9%. Similarly, the oral care composition comprises 85 to 94% of the total weight of the encapsulated oral care composition, more preferably 88 to 92, and most preferably about 91%.

In one preferred aspect of the invention, the aforementioned encapsulated oral care composition is positioned on an oral care implement. For example, the encapsulated oral care composition can be positioned on the head of the oral care implement. This can be accomplished by positioning the encapsulated oral care composition within or between the cleaning elements of the oral care implement. When applied to such a tooth brushing device, the amount of oral care composition within the capsule typically ranges 45 mg to 80 mg, preferably 50 mg to 75 mg, and most preferably about 64 mg of oral care.

The oral care implement may include a rupturable dispenser containing the oral care composition, as a connected unit or the various other combinations of components and materials as described. A dispenser containing a oral care, such as the oral care composition described herein, or other oral care material can be connected in the bristle or cleaning element portion of the oral care implement for dispensing the oral care composition to the teeth. In one construction, the oral care elements are configured to slow a radial flow of the oral care composition released from the dispenser near an interior region of the carrier and increase a radial flow of the oral care material away from the interior region.

The composition has been described above with respect to several preferred embodiments. Further non-limiting description is provided in the Example that follow.

EXAMPLE

As noted above, the inventors believe that the beneficial effects provided by the invention are related to preventing or delaying migration of cetylpyridinium chloride into the gelatin capsule during the cooling stage of manufacturing, when all layers of the capsule are effectively liquid. Thus, the particle settling times for a series of formulations were studied along with the viscosity of the formulations. The particle settling time for a given formulation should be predictive of the migration of cetylpyridinium chloride from that formulation into a gelatin capsule. Viscosities were measured to identify any relationship between viscosity and particle settling time. The viscosity was measured using a viscometer model, Brookfield LVDV 2+. A V73 type spindle was used. Viscosity values were measured at 1 rpm.

These values were compared with a reference sample, WISP™ PLUS WHITENING, which has a viscosity of 317 cps and has a particle settling time of 20 minutes. However, upon use of CPC, the particle settling time is insufficient to avoid the aforementioned problems caused by the rapid migration of cetylpyridinium chloride into a gelatin capsule. Particle settling time was determined by visually monitoring the migration of suspended powdered particles to the bottom of a vessel. A stop watch was utilized to record the time it took for the powder particles to completely settle to the bottom of the vessel.

Thus, test formulations were evaluated relative to the reference (control) formulation. The results are given in Table I below. Test formulations with particle settling times longer than 10 minutes and with viscosities equal to or less than about 800 cps are ideal. These formulations will prevent the cetylpyridinium chloride from substantially migrating into the gelatin capsule during the cooling/solidifying stage of the capsule production, but have a viscosity sufficiently low such that they are amenable to current processing conditions. Table I shows that several of the test formulations have viscosities within the preferred range below 800 cps or below 750 cps or below 500 cps or less than or equal to 350 cps or 100-800 cps or 150-750 cps.

TABLE 1

Suspension of CPC with Plastigel DOE

| Ingredients | Control | 0% | 2% | 4% | 8% | 12% | 14% | 18% |
|---|---|---|---|---|---|---|---|---|
| Caprylic/capric triglyceride | 75.5 | 84.25 | 82.25 | 80.25 | 76.25 | 72.25 | 70.25 | 66.25 |
| CPC | x | 0.75 | 0.75 | 0.75 | 0.75 | 0.75 | 0.75 | 0.75 |
| Plastigel | x | 0 | 2 | 4 | 8 | 12 | 14 | 18 |
| Flavor | 15 | 15 | 15 | 15 | 15 | 15 | 15 | 15 |
| Sucralose + EtOH | 4.5 | x | x | x | x | x | x | x |
| AC 43 Silica | 5 | x | x | x | x | x | x | x |
| Total | 100 | 100 | 100 | 100 | 100 | 100 | 100 | 100 |
| Viscosity, cps | 327 | x | 189 | 238 | 238 | 345 | 357 | 1011 |
| Settling time, min | 20 | 4 | 2.5 | 90 | 150 | 240 | 72 hrs | 1 week |

The invention has been described above with respect to various preferred aspects; however it is to be understood the invention is not limited to the disclosed embodiments. Variations and modifications that will occur to the person of skill in the art are also part of the invention, which is defined in the appended claims.

What is claimed is:

1. An encapsulated oral care composition comprising:
   (a) a water soluble capsule; and
   (b) an oral care composition contained within the capsule, and comprising:
      i. a hydrophilic active;
      ii. a hydrophobic structuring agent; and
      iii. a hydrophobic carrier;
   wherein the hydrophobic structuring agent comprises a gelled mineral oil and is present in an amount of 1-20 wt. % based on a total weight of the oral care composition; and
   wherein the hydrophilic active is cetylpyridinium chloride, and wherein the gelled mineral oil comprises polyethylene and mineral oil.

2. The composition of claim 1, wherein the hydrophilic active comprises a solid active.

3. The composition of claim 1, wherein the carrier comprises at least one of a vegetable oil and silicone oil.

4. The composition of claim 1, wherein the carrier comprises a C6 to C12 triglyceride.

5. The composition of claim 1, wherein the carrier constitutes 60-80 wt. % of the oral care composition.

6. The composition of claim 1, wherein the hydrophilic active constitutes 0.05-5 wt. % of the oral care composition.

7. The composition of claim 1, wherein the oral care composition further comprises 5-25 wt. % of a flavoring agent and 0.1-5 wt. % of a sweetening agent.

8. The composition of claim 1, wherein the carrier is caprylic/capric triglyceride and the oral care composition further comprises hydrated silica, sorbitol, sucralose, glycerin, a colorant and a flavoring agent.

9. The composition of claim 1, wherein the oral care composition has a viscosity from 150 to 750 cps as measured by a Brookfield LVDV 2+ with V73 spindle at 1 rpm.

10. A oral care implement comprising: a handle; a head mounted to the handle, the head comprising an outer surface and a plurality of tooth cleaning elements extending outwardly from the outer surface; and the composition of any preceding claim positioned on the head.

11. The composition of claim 2, wherein the carrier constitutes 60-80 wt. % of the oral care composition.

12. The composition of claim 11, wherein the carrier comprises at least one of a vegetable oil and silicone oil.

13. The composition of claim 12, wherein the composition has a particle settling time of more than 10 minutes.

14. The composition of claim 13, wherein the cetylpyridinium chloride constitutes 0.05-5 wt. % of the oral care composition, the carrier is caprylic/capric triglyceride, and the oral care composition further comprises hydrated silica, sorbitol, sucralose, glycerin, a colorant and a flavoring agent.

15. The composition of claim 13, wherein the cetylpyridinium chloride constitutes 0.05-5 wt. % of the oral care composition, and the carrier is caprylic/capric triglyceride.

16. The composition of claim 15, wherein the oral care composition has a viscosity from 150 to 750 cps as measured by a Brookfield LVDV 2+ with V73 spindle at 1 rpm.

\* \* \* \* \*